(12) United States Patent
Choi et al.

(10) Patent No.: US 9,402,903 B2
(45) Date of Patent: Aug. 2, 2016

(54) MAGNETIC FIELD-CONTROLLED MOVABLE BIO-SCAFFOLD AND CONSTRUCTING METHOD THEREOF

(71) Applicant: Daegu Gyeongbuk Institute of Science and Technology, Daegu (KR)

(72) Inventors: Hong Soo Choi, Daegu (KR); Sang Won Kim, Daegu (KR)

(73) Assignee: DAEGU GYEONGBUK INSTITUTE OF SCIENCE AND TECHNOLOGY (KR)

( * ) Notice: Subject to any disclaimer, the term of this patent is extended or adjusted under 35 U.S.C. 154(b) by 22 days.

(21) Appl. No.: 13/998,534

(22) Filed: Nov. 7, 2013

(65) Prior Publication Data

US 2014/0302110 A1  Oct. 9, 2014

(30) Foreign Application Priority Data

Apr. 8, 2013 (KR) .................. 10-2013-0037960

(51) Int. Cl.
*A61K 41/00* (2006.01)

(52) U.S. Cl.
CPC ..................... *A61K 41/00* (2013.01)

(58) Field of Classification Search
CPC ..................................................... A61K 41/00
See application file for complete search history.

(56) References Cited

U.S. PATENT DOCUMENTS

| | | | |
|---|---|---|---|
| 4,335,094 A * | 6/1982 | Mosbach ..................... | 424/1.37 |
| 5,412,727 A | 5/1995 | Drexler et al. | |
| 6,412,692 B1 | 7/2002 | Miyagawa | |
| 6,540,138 B2 | 4/2003 | Hall et al. | |
| 7,377,430 B2 | 5/2008 | Fleischman | |
| 7,422,150 B2 | 9/2008 | Chung | |
| 7,431,209 B2 | 10/2008 | Chung | |
| 7,637,429 B2 | 12/2009 | Cordery et al. | |
| 7,861,918 B2 | 1/2011 | Strabone | |
| 2002/0074399 A1 | 6/2002 | Hall et al. | |
| 2002/0187172 A1* | 12/2002 | Reb et al. ..................... | 424/401 |
| 2004/0105980 A1* | 6/2004 | Sudarshan et al. ............ | 428/404 |
| 2005/0218224 A1 | 10/2005 | Boldin | |
| 2006/0196939 A1 | 9/2006 | Kim et al. | |
| 2012/0053997 A1 | 3/2012 | Garfinkle et al. | |

FOREIGN PATENT DOCUMENTS

| | | |
|---|---|---|
| CA | 2 772 649 | 3/2011 |
| EP | 1 291 826 | 12/2003 |
| WO | 2004 038632 | 5/2004 |
| WO | 2011 071401 | 6/2011 |

OTHER PUBLICATIONS

Bosnjak et al. (Am J Physiol Heart Circ Physiol 2003; 284:H1080-1086).*
Philippova et al. (European Polymer Journal 2011;47:542-559).*
Wong et al. (Journal of Magnetism and Magnetic Materials 2007;311:219-223).*
Trechsel, A.H., Alvarez, R.M., Hall, T.E., "Internat Voting in Estonia," Caltech/MIT Voting Technology Project, Jan. 2008.
Department of Defence, Washington Headquarters Services Federal Voting Assistance Program, "Voting over the Internet Pilot Project Assessment Report," Jun. 2001.
Kim, S., Qui, F., Zhang, L., Nelson, B., Choi, H., "Fabrication and Control of Microrobots for Targeted Cell Transportation," International Symposium on Nature-Inspired Technology, 2013.

* cited by examiner

*Primary Examiner* — Ernst V Arnold
(74) *Attorney, Agent, or Firm* — Emerson Thomson Bennett, LLC; Daniel A. Thomson

(57) ABSTRACT

Disclosed are a magnetic field-controlled movable bio-scaffold and a method for constructing the same. The bio-scaffold is highly biocompatible and can readily move to a target site under the control of an external magnetic field.

14 Claims, 5 Drawing Sheets

(a) Glass wafer (d) Baking (b) SU-8 coating, baking (e) Development (c) Laser exposure (scanning)

(f) Nickel, titanium deposition

MAGNETIC FIELD-CONTROLLED MOVABLE BIO-SCAFFOLD AND CONSTRUCTING METHOD THEREOF

BACKGROUND OF THE INVENTION

1. Field of the Invention

The present invention relates to a movable bio-scaffold and a method for constructing the same. More particularly, the present invention relates to a bio-scaffold which can move to a target site under the control of an external magnetic field, and a method for constructing the same.

2. Description of the Related Art

In recent years, great progress has been made in the bioengineering field, particularly, tissue engineering. Tissue engineering is an interdisciplinary field that applies the principles of engineering and life sciences toward the development of biological substitutes that restore, maintain or improve tissue function or a whole organ, based on the understanding of relationship between structures and functions of tissues.

In spite of the rapid development of medical engineering to a high level, organ transplantation, which is for the purpose of replacing damaged or absent organs, which frequently occur, still remains difficult, with various problems including high cost, deficiency of donors, and side effects associated with the use of immunosuppressants.

The development of artificial organs or the regeneration of tissues, based on tissue engineering, has been emerging as a new approach to organ transplantation. Tissue engineering is fundamentally focused on the implantation of a cell-scaffold complex to a patient which is fabricated by taking a necessary tissue from the patient, isolating cells from the tissue, and culturing the cells on the scaffold.

For use in biological application, the scaffold should meet various requirements as well as safety in the body. A scaffold must be formed of a material helpful for the attachment, growth, and differentiation of cells, and a porous structure must be formed across the scaffold so that cell growth and tissue regeneration can be facilitated therein. Further, high interconnection should be established among pores of the porous structure. In addition to having biocompatibility, a bio-scaffold should be of porosity so that it provides a large surface area to facilitate the integration of cells to be implanted into a tissue. According to the site where to apply, the bio-scaffold may be formed of a biodegradable material. Most of currently used bio-scaffolds are applied mainly to the regeneration of the bone, the skin, and organs. Morphologies and pore sizes of the bio-scaffolds are determined according to the cells and tissues to be implanted thereinto. Porosities, pore sizes, and three-dimensional interconnection of multiple spaces of bio-scaffolds are very important factors because they have great influence on the establishment of new tissues in the bio-scaffolds. A porous structure is necessary for carrying a sufficient number of cells while an interconnected porous syntax is responsible for the diffusion of nutrients.

Research and development has recently continued to be directed toward the preparation of bio-scaffolds which can be stably used for the therapy and regeneration of tissues.

Conventional scaffolds are, however, disadvantageous in terms of insertion into the body localization to a target site. For example, they are inserted directly into the body and localized at a target site, mostly with the aid of surgery and mechanical instrument, which may give rise to the likelihood of infection and injury during the insertion. In addition, a limitation is imposed on the application of conventional scaffolds to local sites difficult to approach, or sites which become in danger upon external exposure, such as vessels and cerebral tissues.

SUMMARY OF THE INVENTION

Accordingly, the present invention has been made keeping in mind the above problems occurring in the prior art, and an object of the present invention is to provide a magnetic field-controlled movable bio-scaffold which is highly biocompatible and can be readily translocated to a target site within the body under the control of an external magnetic field, and a method for constructing the same.

In order to accomplish the above object, the present invention provides a magnetic field-controlled movable bio-scaffold, comprising a porous bio-scaffold; and a magnetic layer applied to the bio-scaffold.

In one preferred embodiment of the present invention, the magnetic field-controlled movable bio-scaffold may further comprise a biocompatible metal layer applied to the magnetic layer.

In another preferred embodiment of the present invention, the magnetic field-controlled movable bio-scaffold may further comprise cells cultured in pores thereof.

In a further preferred embodiment of the present invention, the porous bio-scaffold may have a three-dimensional structure composed of a photocurable polymer.

In a still further preferred embodiment of the present invention, the porous bio-scaffold may be in a form of a cylinder, a hexahedron, an ellipsoid, a polyhedron, or a circular cone.

In still another preferred embodiment of the present invention, the porous bio-scaffold may have a circular section on any one of XY, YZ and XZ coordinate planes in the Cartesian coordinates.

In yet another preferred embodiment of the present invention, the porous bio-scaffold may have a rectangular section on any one of XY, YZ and XZ coordinate planes in the Cartesian coordinates.

In a yet further preferred embodiment of the present invention, the porous bio-scaffold may have a triangular section on any one of XY, YZ and XZ coordinate planes in the Cartesian coordinates.

Also, the present invention provides a method for translocating the magnetic field-controlled movable bio-scaffold to a target site under the control of an external magnetic field.

Further, the present invention addresses a method for constructing a magnetic field-controlled movable bio-scaffold, comprising: (1) fabricating a porous bio-scaffold type structure; and (2) coating the porous bio-scaffold type structure with a magnetic material.

In one preferred embodiment of the present invention, step (1) is carried out by lithography using a photocurable polymer to afford a three-dimensional bio-scaffold type structure.

In another preferred embodiment of the present invention, the method may further comprise (3) applying a biocompatible metal to the magnetic material after step (2).

In a further preferred embodiment of the present invention, the method may further comprise (4) culturing cells within pores of the metal-coated bio-scaffold after step (3).

In a still further preferred embodiment of the present invention, the three-dimensional bio-scaffold type structure is in a form of a cylinder, a hexahedron, an ellipsoid, a polyhedron, or a circular cone.

Configured to readily move to a target site under the control of an external magnetic field in addition to being of high biocompatibility, the magnetic field-controlled movable bio-scaffold of the present invention can be positioned at local sites difficult to approach, or sites which become in danger upon external exposure, such as vessels and cerebral tissues, while avoiding direct insertion into a desired site with the aid of surgery and mechanical instrument.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
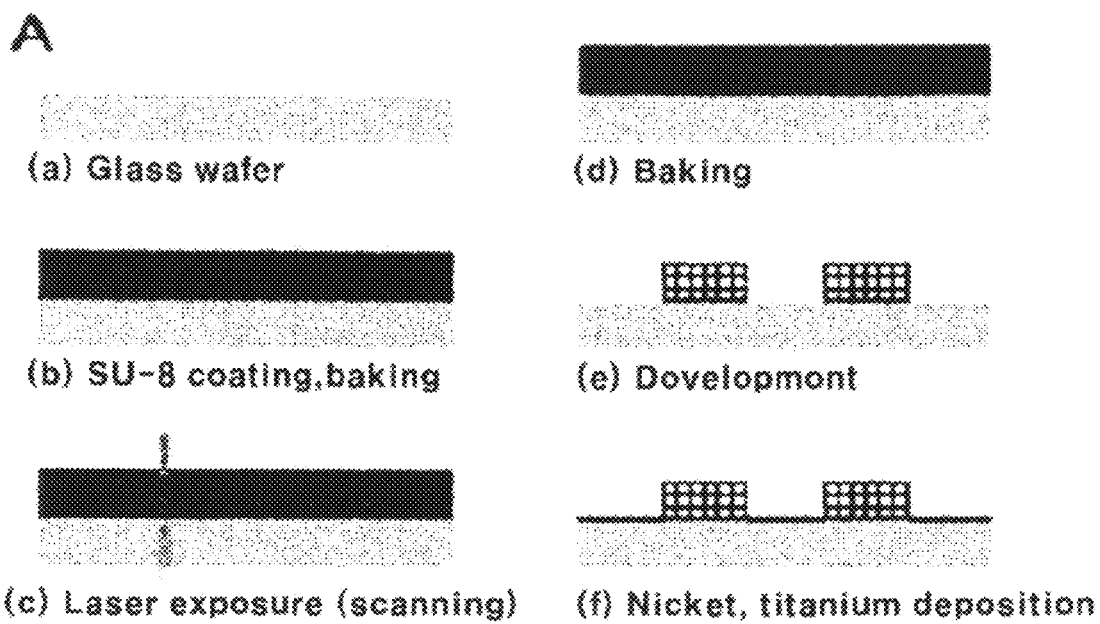
FIG. 1 is a process flow illustrating the construction of a magnetic field-controlled movable bio-scaffold according to one preferred embodiment of the present invention.
Figure 2:
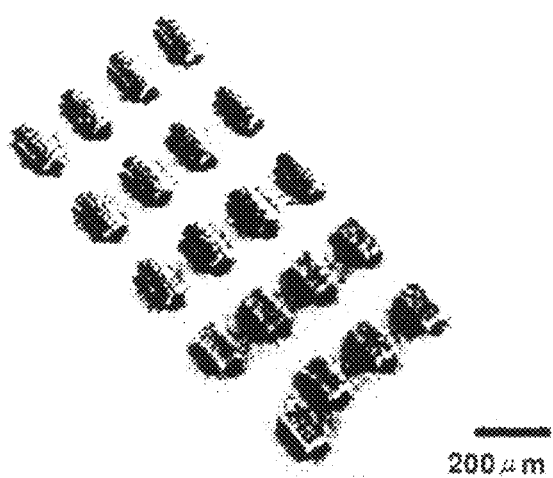
FIG. 2 is an SEM image of magnetic field-controlled movable bio-scaffolds constructed in Example 1 or 2.

Below, a detailed description will be given of the present invention, with reference to the drawings.

As aforementioned, conventional bio-scaffolds suffer from the disadvantage of being inserted directly into a target site and being fixedly positioned thereat, with the aid of surgery and mechanical instrument. In addition, conventional bio-scaffolds are limitedly applied to local sites difficult to approach, or sites which become in danger upon external exposure, such as vessels and cerebral tissues.

To overcome problems encountered in the prior art, the present invention provides a magnetic field-controlled movable bio-scaffold comprising a porous bio-scaffold; and a magnetic layer applied to the bio-scaffold.

The bio-scaffold is of high biocompatibility and is allowed to readily move to a target site in the presence of an external magnetic field.

Structured to have a porous type structure coated with a magnetic material, the magnetic field-controlled movable bio-scaffold of the present invention can be translocated to a target site by an external magnetic field.

So long as it is used as a typical bio-scaffold in terms of material and morphology, any porous bio-scaffold may be employed without limitations. For example, the porous bio-scaffold of the present invention may be prepared from a polymer, a ceramic, a nanofiber, a phospholipid layer, or a biocompatible metal and in a three-dimensional structure as well as in a two-dimensional structure.

Preferably, the porous bio-scaffold may have a 3D structure, formed of a photocurable polymer, which advantageously encourages the migration and infiltration of cells. In a more preferred embodiment, the porous bio-scaffold may be constructed in such a microsized, 3D structure from a photocurable polymer by lithography that it can easily move within the body.

The photocurable polymer is a polymer which is cured upon exposure to light, and is not imposed with any limitation so long as it can be constructed into a three-dimensional bio-scaffold by lithography. Preferred may be one selected from among SU-8 polymer, KNPR, IP-L, IP-G, and a combination thereof, with most preference for SU-8 polymer.

Morphologically, the 3D bio-scaffold may vary depending on the type of the cells and tissues to be implanted. Although no special morphological limitations are imposed thereto, the 3D bio-scaffold of the present invention may be in the form of a cylinder, a hexahedron, an ellipsoid, a polyhedron, or a circular cone.

In addition, the 3D bio-scaffold of the present invention may be in a dual or more morphological structure. That is, one selected from among cylindrical, hexahedral, ellipsoidal, polyhedral, and circular conical structures may be present, in combination with a different one selected from thereamong, in the 3D bio-scaffold of the present invention. For example, a 3D bio-scaffold in which a first cylindrical structure is conjugated with a second spiral structure, or in which a first hexahedral structure is conjugated with a second wave-type hexahedral structure smaller in width or length distance than the first structure may be constructed.

Further, the 3D bio-scaffold may have a circular, rectangular or triangular section on any one of XY, YZ and XZ coordinate planes in the Cartesian coordinates.

In one preferred embodiment of the present invention, when the 3D bio-scaffold has a circular section on one of the XY, YZ and XZ planes in the Cartesian coordinates, the area of the section may range from 3.14 to 785,000 $\mu m^2$.

In another preferred embodiment of the present invention, when the 3D bio-scaffold has a rectangular section on any one of XY, YZ and XZ planes in the Cartesian coordinates, the area of the section may be on the order of 1 to $1 \times 10^6$ $\mu m^2$.

In a further preferred embodiment of the present invention, when the 3D bio-scaffold has a triangular section on any one of XY, YZ and XZ planes in the Cartesian coordinates, the area of the section may be on the order of 0.5 to $5 \times 10^5$ $\mu m^2$.

No size limitations are imposed to the 3D bio-scaffold which is small enough to move within the body after introduction into the body. Preferably, the 3D bio-scaffold is 1 to 1,000 $\mu m$ long in width, length or diameter, with a height of 1 to 1,000 $\mu m$, and more preferably 10 to 300 $\mu m$ long in width, length or diameter, with a height of 10 to 300 $\mu m$. When the dimensions of the bio-scaffold meet the condition, it may readily move within the body in the presence of an external magnetic field, and effectively swim in vessels, cerebral ventricles, and viscoelastic media and fluid of organs. For example, the 3D bio-scaffold in a cylindrical structure of Example 1 was 75 $\mu m$ long in diameter with a height of 150 $\mu m$. For a hexahedron of Example 2, dimensions of 75 $\mu m$ width×75 $\mu m$ length×150 $\mu m$ height were measured.

In addition, the porous bio-scaffold may vary in mean pore size depending on the type of the cells and tissues to be implanted. However, no particular limitations are imposed to the mean pore size. Preferably, it may range from 5 to 30 $\mu m$, and more preferably from 10 to 20 $\mu m$.

As mentioned above, the porous bio-scaffold of the present invention includes a magnetic layer applied to the scaffold type structure. Coated with a magnetic material, the bio-scaffold can move under the control of an external magnetic field. Accordingly, the bio-scaffold can be positioned at a target site even if it is not inserted directly to the target site with the aid of surgery or mechanical instrument. In case where the porous bio-scaffold is not coated with a magnetic material, but contains magnetic particles therein, it is difficult not only to control the migration of the bio-scaffold with an external magnetic field, but also to construct a bio-scaffold in a 3D structure using lithography. Since magnetic particles, which do not allow for light transmission, increase optical inference upon irradiation, the scaffold type structure containing magnetic particles is difficult to construct into a desired 3D morphological structure by lithography. For example, the constructed bio-scaffold may be not morphologically smooth, but irregular, with random pores in size and alignment. Lithography is preferable for constructing micro-sized, 3D bio-scaffolds that can readily move within the body in the presence of an external magnetic field. Hence, lithography is not suitable for the construction of a bio-scaffold containing magnetic particles.

So long as it is magnetic without significant corrosiveness (reactivity), any metal may be used for the coated magnetic layer without particular limitation. More preferable examples of the magnetic material include nickel (Ni), iron (Fe), cobalt (Co), neodymium (Nd), and a combination thereof, with most preference for nickel (Ni).

If it allows for the free movement of the bio-scaffold within the body in the presence of an external magnetic field, the thickness of the magnetic layer is not particularly limited. Preferably, the magnetic layer is 50 to 200 nm thick, and more preferably 100 to 200 nm thick. For example, when the magnetic field is less than 50 nm in thickness, the magnetism is so slight that it is difficult to control the movement of the bio-scaffold within the body by an external magnetic field. On the other hand, when the thickness of the magnetic field exceeds 200 nm, it took a long period of time to deposit the magnetic layer. In this case, additionally, since the thick magnetic layer is not clearly separated from the structure, the surface of the bio-scaffold is not smooth, and the magnetic layer is not uniformly deposited on the photocurable polymer. Also, the thick magnetic layer is apt to detach from the photocurable polymer in its entirety.

Moreover, the magnetic field-controlled movable bio-scaffold may further comprise a biocompatible metal layer on the coated magnetic layer so as to improve in biostability and biocompatibility.

So long as it is stable within the body, and exhibits high biocompatibility, any metal may be used in the biocompatible metal layer. More preferred is titanium (Ti), medical stainless steel, alumina ($Al_2O_3$), gold (Au), or a combination thereof, with most preference for titanium (Ti).

Unless it degrades the biocompatibility of the bio-scaffold, the thickness of the biocompatible metal layer is not particularly limited. Preferably, the biocompatible layer may be 10 to 50 nm thick. For example, when the magnetic field is less than 10 nm in thickness, the biocompatibility may be significantly degraded. On the other hand, when the thickness of the magnetic field exceeds 50 nm, it took a long period of time to deposit the biocompatible layer. In this case, since the thick biocompatible metal layer is not clearly separated from the structure, the surface of the bio-scaffold is not smooth, and the biocompatible metal layer is not uniformly deposited on the magnetic layer.

In addition, the magnetic field-controlled movable bio-scaffold may further comprise cells cultured within the pores. Cells, whether the same or different, may be cultured within the pores of the magnetic field-controlled movable bio-scaffold to form a cell-scaffold complex which can be introduced into the body and move to a target site under the control of an external magnetic field.

Also, contemplated in accordance with an aspect of the present invention is a drug carrier comprising a drug; and the movable bio-scaffold with the drug loaded thereto.

The movable bio-scaffold may comprise a porous bio-scaffold type structure; and a magnetic layer applied to the bio-scaffold type structure, and is allowed to move to a desired position due to a magnetic layer formed on the porous bio-scaffold type structure under the control of an external magnetic field.

So long as it is used as a typical bio-scaffold in terms of material and morphology, any porous bio-scaffold type structure may be employed without limitations. For example, the porous bio-scaffold of the present invention may be prepared from a polymer, a ceramic, a nanofiber, a phospholipid layer, or a biocompatible metal.

In addition, the movable bio-scaffold may further a biocompatible metal layer applied to the magnetic layer.

Moreover, the porous bio-scaffold may have a 3D structure, formed of a photocurable polymer, which advantageously encourages the migration and infiltration of cells. The 3D bio-scaffold of the present invention may be in the form of a cylinder, a hexahedron, an ellipsoid, a polyhedron, or a circular cone.

So long as it is typically applied to organisms, any drug can be contained in the drug carrier. Examples of the drug include vasodilators, anti-inflammatory agents, luteinizing hormone, antidiabetics, angiogenesis inhibitors, gene silencers, AIDS vaccines, and influenza vaccines.

The drug loaded into the drug carrier can exert its pharmaceutical effect on a target site through diffusion upon the destruction or disruption of a coating layer or capsule surrounding the drug by ultrasonication and/or heating after the drug carrier is driven to the target site by an external magnetic field.

In addition, the present invention addresses a method for moving the magnetic field-controlled movable bio-scaffold to a target site under the control of an external magnetic field.

Figure 5:
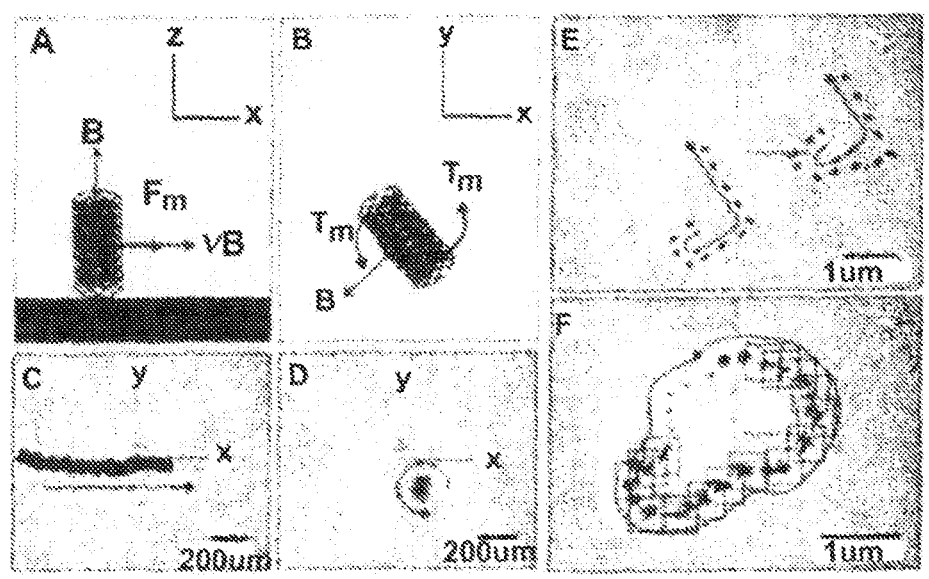
FIG. 5 show control modes of the motion of a magnetic field-controlled movable bio-scaffold according to one preferred embodiment of the present invention.

Referring to FIG. 5, there are the magnetic field-controlled movable bio-scaffolds of the present invention that are under the control of a magnetic field. As shown in FIG. 5, the magnetic field-controlled movable bio-scaffold of the present invention can move straightly (A: principle of rectilinear motion, C: captured image of the bio-scaffold in rectilinear motion) and rotationally (B: principle of rotational motion, D: captured image of the bio-scaffold in rotational motion) in the presence of an external magnetic field. Various combinations of these motions enable the bio-scaffold to run along three-dimensional complicate passages in a control mode (E: simultaneous control, F: tracking a target site). Therefore, the bio-scaffold of the present invention needs not to be inserted directly into a target site by surgery and with the aid of mechanical instrument, and can be positioned even at sites which fall in danger upon external exposure, such as vessels and cerebral tissues, under the control of an external magnetic field without risk of infection and injury.

Also, the present invention addresses a method for constructing the magnetic field-controlled movable bio-scaffold, comprising: (1) fabricating a porous bio-scaffold; and (2) coating the porous bio-scaffold with a magnetic material.

In detail, step (1) is to fabricate a porous bio-scaffold.

The fabrication of a porous bio-scaffold may be accomplished using a typical process. Representative among the process are particulate leaching, emulsion freeze-drying, high pressure gas expansion and phase separation, FDM (fused deposition modeling), and lithography.

So long as it is found in a typical bio-scaffold, any material may be employed in the porous bio-scaffold of the present invention without limitations. For example, the porous bio-scaffold of the present invention may be prepared from a polymer, a ceramic, a nanofiber, a phospholipid layer, or a biocompatible metal and in a three-dimensional structure as well as in a two-dimensional structure.

In the present invention, a three-dimensional bio-scaffold which can readily move within the body under the control of an external magnetic field may be constructed from a photocurable polymer by lithography. The 3D structure advantageously encourages the migration and infiltration of cells. In a more preferred embodiment, the porous bio-scaffold may be constructed in such a microsized, 3D structure from a photocurable polymer by lithography that it can easily move within the body.

The photocurable polymer is a polymer which is cured upon exposure to light, and is not imposed with any limitation so long as it can be constructed into a three-dimensional bio-scaffold by lithography. Preferred may be one selected from among SU-8 polymer, KMPR, IP-L, IP-G, and a combination thereof, with most preference for SU-8 polymer.

Morphologically, the 3D bio-scaffold may vary depending on the type of the cells and tissues to be implanted. Although no special morphological limitations are imposed thereto, the 3D bio-scaffold of the present invention may be in the form of a cylinder, a hexahedron, an ellipsoid, a polyhedron, or a circular cone.

Further, the 3D bio-scaffold may have a circular, rectangular or triangular section on any one of XY, YZ and XZ coordinate planes in the Cartesian coordinates.

In one preferred embodiment of the present invention, when the 3D bio-scaffold has a circular section on any one of the XY, YZ and XZ planes in the Cartesian coordinates, the area of the section may range from 3.14 to 785,000 $\mu m^2$.

In another preferred embodiment of the present invention, when the 3D bio-scaffold has a rectangular section on any one of XY, YZ and XZ planes in the Cartesian coordinates, the area of the section may be on the order of 1 to $1\times10^6$ $\mu m^2$.

In a further preferred embodiment of the present invention, when the 3D bio-scaffold has a triangular section on any one of XY, YZ and XZ planes in the Cartesian coordinates, the area of the section may be on the order of 0.5 to $5\times10^5$ $\mu m^2$.

No size limitations are imposed to the 3D bio-scaffold which is small enough to move within the body after introduction into the body. Preferably, the 3D bio-scaffold is 1 to 1,000 µm long in width, length or diameter, with a height of 1 to 1,000 µm, and more preferably 10 to 300 µm long in width, length or diameter, with a height of 10 to 300 µm. When the dimensions of the bio-scaffold meet the condition, it may readily move within the body in the presence of an external magnetic field, and effectively swim in vessels, cerebral ventricles, and viscoelastic media and fluid of organs.

In addition, the porous bio-scaffold may vary in mean pore size depending on the type of the cells and tissues to be implanted. However, no particular limitations are imposed to the mean pore size. Preferably, it may range from 5 to 30 µm, and more preferably from 10 to 20 µm.

The 3D bio-scaffold can be fabricated in such a way that its size and porosity fall within the above range by controlling parameters of lithography including light intensity, scan speed, slice distance, etc.

Next, step (2) is to coat the fabricated porous bio-scaffold with a magnetic material.

Coated with a magnetic material, the bio-scaffold can move under the control of an external magnetic field. Accordingly, the bio-scaffold can be positioned at a target site even if it is not inserted directly to the target site with the aid of surgery or mechanical instrument. In case where the porous bio-scaffold is not coated with a magnetic material, but contains magnetic particles therein, it is difficult not only to control the migration of the bio-scaffold with an external magnetic field, but also to construct a bio-scaffold in a 3D structure using lithography. Since magnetic particles, which do not allow for light transmission, increase optical inference upon irradiation, the scaffold type structure containing magnetic particles is difficult to construct into a desired 3D morphological structure by lithography. For example, the constructed bio-scaffold may be not morphologically smooth, but irregular, with random pores in size and alignment. Lithography is preferable for constructing microsized, 3D bio-scaffolds that can readily move within the body in the presence of an external magnetic field. Hence, lithography is not suitable for the construction of a bio-scaffold containing magnetic particles.

So long as it is magnetic without significant corrosiveness (reactivity), any metal may be used for the coated magnetic layer without particular limitation. More preferable examples of the magnetic material include nickel (Ni), iron (Fe), cobalt (Co), neodymium (Nd), and a combination thereof, with most preference for nickel (Ni).

Any coating method which is typical in the art may be employed to apply a magnetic material to the porous bio-scaffold, without limitations. Preferred is electron beam deposition, dipping, electropolating, sputtering, or chemical vapor deposition.

If it allows for the free movement of the bio-scaffold within the body in the presence of an external magnetic field, the thickness of the magnetic layer is not particularly limited. Preferably, the magnetic layer is 50 to 200 nm thick, and more preferably 100 to 200 nm thick. For example, when the magnetic field is less than 50 nm in thickness, the magnetism is so slight that it is difficult to control the movement of the bio-scaffold within the body by an external magnetic field. On the other hand, when the thickness of the magnetic field exceeds 200 nm, it took a long period of time to deposit the magnetic layer. In this case, additionally, since the thick magnetic layer is not clearly separated from the structure, the surface of the bio-scaffold is not smooth, and the magnetic layer is not uniformly deposited on the photocurable polymer. Also, the thick magnetic layer is apt to detach from the photocurable polymer in its entirety Optionally, the method for constructing the magnetic field-controlled movable bio-scaffold in accordance with the present invention may further comprise (3) coating the magnetic material-coated porous bio-scaffold with a biocompatible metal to enhance in vivo stability and biocompatibility of the bio-scaffold.

So long as it is stable within the body, and exhibits high biocompatibility, any metal may be used in the biocompatible metal layer. More preferred is titanium (Ti), medical stainless steel, alumina ($Al_2O_3$), gold (Au), or a combination thereof, with most preference for titanium (Ti).

Like the coating of the magnetic material, electron beam deposition, dipping, electroplating, sputtering or chemical vapor deposition may be used to apply the biocompatible metal to the bio-scaffold.

Unless it degrades the biocompatibility of the bio-scaffold, the thickness of the biocompatible metal layer is not particularly limited. Preferably, the biocompatible layer may be 10 to 50 nm thick. For example, when the magnetic field is less than 10 nm in thickness, the biocompatibility may be significantly degraded. On the other hand, when the thickness of the magnetic field exceeds 50 nm, it took a long period of time to deposit the biocompatible layer. In this case, since the thick biocompatible metal layer is not clearly separated from the structure, the surface of the bio-scaffold is not smooth, and the biocompatible metal layer is not uniformly deposited on the magnetic layer.

A better understanding of the present invention may be obtained through the following examples which are set forth to illustrate, but are not to be construed as limiting the present invention.

Example 1

Construction of Magnetic Field-Controlled, Movable Cylindrical Bio-Scaffold

A 3-cm glass wafer was cleaned using isopropyl alcohol (IPA) in an ultrasonication bath to remove dusts and organic material residues therefrom. The wafer was spin-coated with 1.25 ml of SU-8 (NANO™ SU-8 100, Microchem) at 100 rpm/s with an increment up to 500 rpm for 10 sec, and then at 300 rpm/s with an increment up to 1000 rpm for 30 sec. As a result, an SU-8 layer 100 μm thick was formed on the glass water. Subsequently, it was treated at 65° C. for 10 min on a hot plate, and then at 95° C. for 30 min, followed by cooling to the room temperature for 10 min.

Next, two-photon polymerization (TPP) 3D laser lithography was conducted to polymerize a designed structure. The lithography was set forth at a laser intensity of 16% of the maximum laser intensity (20 mW/sec), a scan speed of 50 μm/s, and a slice distance of 0.9 μm. Thereafter, the glass plate was allowed to undergo a thermal treatment at 65° C. for 1 min on a hot plate, and then at 95° C. for 10 min.

After the sample was cooled, SU-8 was developed for 20 min using mr-Dev 600 to afford a cylindrical porous bio-scaffold 75 μm and 150 μm long in diameter and height, respectively, with a pore size of 10~20 μm.

A multiple layer structure consisting of a magnetic layer (Ni) and a biocompatible metal layer (Ti) was formed on the scaffold. First, the scaffold was tilted for uniform deposition, after which E-beam evaporation system with a rotating chuck was used to form a 150 nm-thick Ni layer on the scaffold. Subsequently, the magnetic layer-deposited bio-scaffold was coated with titanium (Ti) to form a biocompatible metal layer 20 μm thick.

Figure 3:
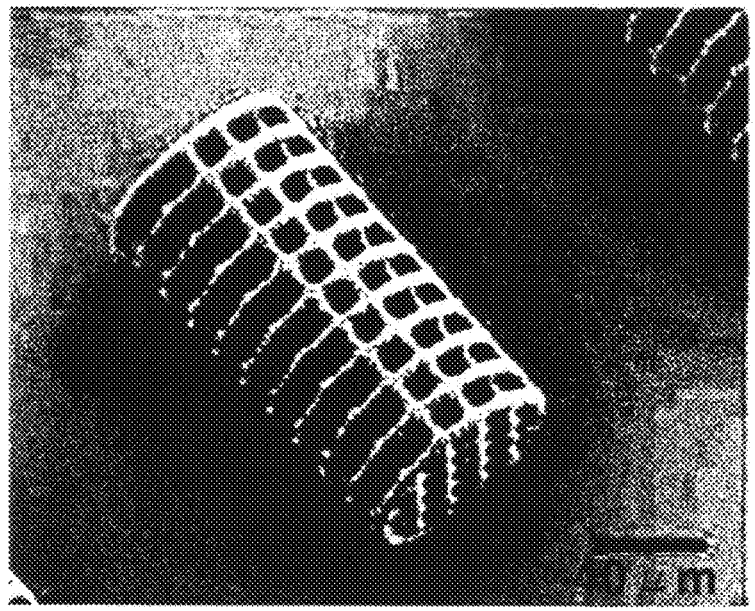
FIG. 3 is an enlarged SEM image of a magnetic field-controlled movable bio-scaffold constructed in Example 1.

An SEM image of the magnetic field-controlled movable bio-scaffold thus constructed is shown in FIG. 3.

Example 2

Construction of Magnetic Field-Controlled, Movable Hexahedral Bio-Scaffold

The same procedure as in Example 1 was carried out to construct a porous bio-scaffold which was 75 μm wide, 75 μm long and 150 μm high with a pore size of 10~20 nm, with the exception that lithography was set forth at a laser intensity of 16% of the maximum laser intensity (20 mW/sec), a scan speed of 50 μm and a slice distance of 0.9 μm.

Figure 4:
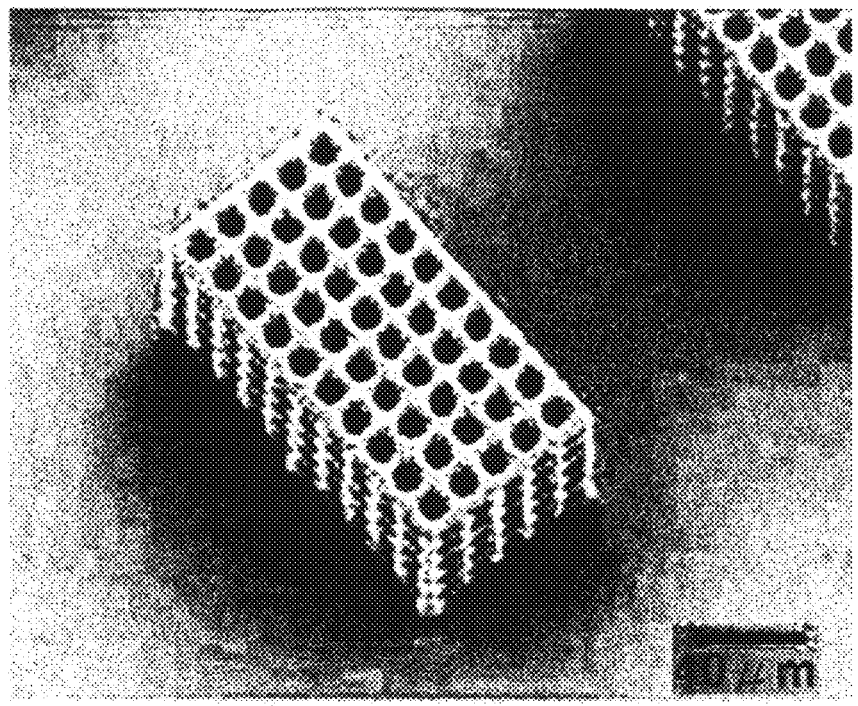
FIG. 4 is an enlarged SEM image of a magnetic field-controlled movable bio-scaffold constructed in Example 2.

An SEM image of the magnetic field-controlled movable bio-scaffold is shown in FIG. 4.

Example 3

Cell Culturing in Magnetic Field-Controlled Movable Bio-Scaffold

Before cell culturing, the bio-scaffold constructed on a glass wafer was sterilized by autoclaving and coated with 10 μm/ml poly L lysine (PLL, 0.01%; Sigma Chemical Co., St. Louis, Mo., USA) which was previously sterilized by UV light.

For use in cell culture in the bio-scaffold, HEK293 (human embryonic kidney 293) cells were maintained in Dulbecco's Modification of Eagle's medium (DMEM) supplemented with 10% fetal bovine serum (SH30919.03, Thermo, USA) and 1% antibiotics, at 37° C. under an atmosphere of 5% $CO_2$. After removal of the medium, the cells were incubated at 37° C. for 30 sec with 0.25% (wt/vol) trypsin in EDTA (ethylenediamine tetraacetic acid), followed by centrifugation for 5 min at 1,000 rpm. The cell pellet thus obtained was suspended at a density of $1\times10^6$ cells/ml in a medium.

The cells in suspension were grown in a medium containing the magnetic field-controlled movable bio-scaffold for 4 days, after which the medium was removed and the dish was washed with dPBS (distilled phosphate buffered solution). Then, the cells were incubated at 4° C. for 24 hrs in 4% paraformaldehyde. The paraformaldehyde was removed before the glass wafer was washed three times with dPBS. It was placed in a clean dish and observed by SEM. In this context, the cells were coated with platinum to observe the magnetic field-controlled movable scaffold in which the cells were grown.

Figure 6:
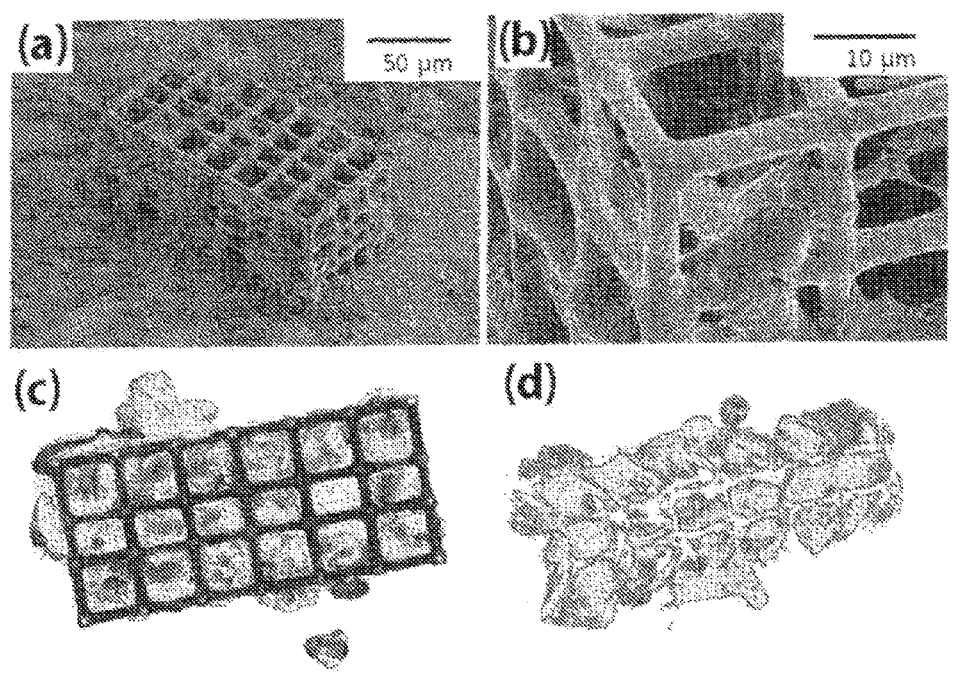
FIG. 6 shows cells cultured in a magnetic field-controlled movable bio-scaffold according to Example 3.

SEM images of the magnetic field-controlled movable bio-scaffolds in which cells have grown are given in FIG. 6. As can be seen, the HEK293 cells are observed to well adhere to the bio-scaffolds, and the magnetic field-controlled movable bio-scaffold is proven to be biocompatible, as demonstrated by the filopodia from the cells.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A drug carrier, comprising:
   a drug; and
   a magnetic field-controlled movable bio-scaffold loaded with the drug, wherein the bio-scaffold has a magnetic layer coating the bio-scaffold, wherein the entire bio-scaffold is coated by the magnetic layer, wherein the magnetic field-controlled movable bio-scaffold is porous, wherein the magnetic layer coated bio-scaffold remains porous.

2. The drug carrier of claim 1, further comprising a biocompatible metal layer formed on the magnetic layer.

3. The drug carrier of claim 1, wherein the porous bio-scaffold structure has a three-dimensional structure composed of a photocurable polymer, wherein the drug is contained within the bio-scaffold.

4. The drug carrier of claim 3, wherein the porous bio-scaffold structure is a cylinder, a hexahedron, an ellipsoid, a polyhedron, or a circular cone.

5. The drug carrier of claim 4, wherein the porous bio-scaffold structure has a circular, rectangular, triangular, or penta- or higher polyhedral section on any one of XY, YZ and XZ coordinate planes in Cartesian coordinates, the sections of XY, YZ and XZ planes being the same or different.

6. The drug carrier of claim 1, wherein the drug is the one selected from vasodilators, anti-inflammatory agents, luteinizing hormone, antidiabetics, angiogenesis inhibitors, gene silencers, AIDS vaccines, influenza vaccines, and a combination thereof.

7. The drug carrier of claim 1, wherein the magnetic layer has the one selected from nickel (Ni), iron (Fe), cobalt (Co), neodymium (Nd), and a combination thereof.

8. The drug carrier of claim 2, wherein the biocompatible metal layer has the one titanium (Ti), medical stainless steel, alumina (Al2O3), gold (Au), and a combination thereof.

9. The drug carrier of claim 1, wherein the bio-scaffold has a width from 1 μm to 1,000 μm and a height from 1 μm to 1,000 μm.

10. The drug carrier of claim 1, wherein the magnetic layer has a thickness from 50 nm to 200 nm.

11. The drug carrier of claim 2, wherein the metal layer has a thickness from 10 nm to 50 nm.

12. The drug carrier of claim 1, wherein the bio-scaffold has a mean pore size from 5 μm to 30 μm.

13. The drug carrier of claim 1, wherein the porous bio-scaffold structure is a hexahedron, an ellipsoid, or a polyhedron.

14. The drug carrier of claim 1, wherein the magnetic layer has the one selected from nickel (Ni), cobalt (Co), neodymium (Nd), and a combination thereof.

\* \* \* \* \*